(12) United States Patent
Nikula et al.

(10) Patent No.: US 11,351,395 B2
(45) Date of Patent: Jun. 7, 2022

(54) MODEL FOR APPLYING RADIATION, METHOD FOR PRODUCING THE SAME, AND USE THEREOF

(71) Applicant: ONCOBETA INTERNATIONAL GMBH, Ravensburg (DE)

(72) Inventors: Tuomo Nikula, Ottobrunn (DE); Thomas Wendler, Munich (DE); Juho Nikula, Munich (DE)

(73) Assignee: ONCOBETA INTERNATIONAL GMBH, Ravensburg (DE)

( * ) Notice: Subject to any disclaimer, the term of this patent is extended or adjusted under 35 U.S.C. 154(b) by 181 days.

(21) Appl. No.: 16/484,495

(22) PCT Filed: Feb. 9, 2018

(86) PCT No.: PCT/EP2018/053329
§ 371 (c)(1),
(2) Date: Aug. 8, 2019

(87) PCT Pub. No.: WO2018/146272
PCT Pub. Date: Aug. 16, 2018

(65) Prior Publication Data
US 2020/0030631 A1 Jan. 30, 2020

(30) Foreign Application Priority Data
Feb. 9, 2017 (DE) ............ 10-2017-102-602.9

(51) Int. Cl.
*A61N 5/10* (2006.01)
*B33Y 10/00* (2015.01)
*B33Y 80/00* (2015.01)

(52) U.S. Cl.
CPC ............ *A61N 5/1028* (2013.01); *B33Y 10/00* (2014.12); *B33Y 80/00* (2014.12)

(58) Field of Classification Search
CPC ...... A61N 5/1028; A61N 5/1001; A61N 5/10; A61N 2005/1094; A61N 2005/1019
See application file for complete search history.

(56) References Cited

U.S. PATENT DOCUMENTS 5,871,708 A * 2/1999 Park ............ A61N 5/1029
424/1.25
6,350,226 B1 2/2002 Fischell et al.
(Continued)

FOREIGN PATENT DOCUMENTS

| CN | 106237547 | 12/2016 |
|----|-----------|---------|
| DE | 102011050848 | 12/2012 |
| WO | WO2015057529 | 4/2015 |

OTHER PUBLICATIONS

International Search Report and Written Opinion for PCT/EP2018/053329 dated May 17, 2018, 14 pages.

*Primary Examiner* — Jacob J Cigna
(74) *Attorney, Agent, or Firm* — Dority & Manning, P.A.

(57) ABSTRACT

A method for producing a model for the application of radiation to a body surface area of a living being for cosmetic or therapeutic purposes is provided. The method includes defining a body surface area to which radiation shall be applied; producing a model having at least one surface which has the inverted shape of the defined body surface area, so that the model is configured to fit on the defined body surface area; and providing a radioactive isotope to the model during its production or after its production. Further, the use of the model in a cosmetic treatment of the skin is provided. The model, for cosmetic or therapeutic purposes, includes a surface which has the inverted shape of a defined body surface area which shall be treated with radiation.

17 Claims, 4 Drawing Sheets

(56) References Cited

U.S. PATENT DOCUMENTS

| | | | |
|---|---|---|---|
| 8,568,693 B2 | 10/2013 | Danikas et al. | |
| 9,486,642 B2 * | 11/2016 | Cipriani | A61P 35/00 |
| 9,849,303 B2 | 12/2017 | English et al. | |
| 10,232,062 B2 | 3/2019 | Stephens et al. | |
| 10,384,078 B2 | 8/2019 | Finger et al. | |
| 10,714,226 B2 | 7/2020 | Vose et al. | |
| 2011/0201866 A1 * | 8/2011 | Cipriani | A61P 35/00 |
| | | | 600/1 |
| 2014/0296609 A1 | 10/2014 | Desantis et al. | |
| 2015/0006098 A1 * | 1/2015 | Ju | G05B 19/41875 |
| | | | 702/84 |
| 2015/0102238 A1 * | 4/2015 | Finger | A61N 5/10 |
| | | | 250/493.1 |
| 2015/0105601 A1 * | 4/2015 | Finger | A61K 51/1251 |
| | | | 600/1 |
| 2015/0105602 A1 | 4/2015 | Finger et al. | |
| 2015/0105605 A1 * | 4/2015 | Finger | A61N 5/1001 |
| | | | 600/3 |
| 2016/0093100 A1 * | 3/2016 | Ju | A61N 5/1007 |
| | | | 700/98 |
| 2017/0361535 A1 * | 12/2017 | Ju | B29C 64/20 |
| 2021/0016106 A1 * | 1/2021 | Majcher | B29C 64/386 |

\* cited by examiner

MODEL FOR APPLYING RADIATION, METHOD FOR PRODUCING THE SAME, AND USE THEREOF

CROSS REFERENCE TO RELATED APPLICATIONS

This application is the U.S. National Stage entry of International Application Number PCT/EP2018/053329 filed under the Patent Cooperation Treaty having a filing date of Feb. 9, 2018, which claims priority to German Patent Application No. 10-2017-102-602.9 having a filing date of Feb. 9, 2017, which are incorporated herein by reference.

TECHNICAL FIELD

The present invention relates to a model, and methods for producing and applying it. The model can be used in a process of applying nuclear radiation to a body surface of a human or of an animal. The application is typically carried out for cosmetic purposes or for medical purposes.

BACKGROUND OF THE INVENTION

It is known that applying nuclear radiation, which is henceforth simply called radiation, from a region outwards of a body towards the human skin achieves a physiological effect. A number of fields are known for which such techniques have been employed. The main purposes are cosmetic, i.e. to alter the structure or appearance of a skin region, and medical, i.e., a lesion on the skin surface or close to it shall be treated by the radiation. Applications where the target is not the skin, but tissue inside a natural orifice or a wound, are also known.

This disclosure deals mainly with the application of beta rays and/or soft gamma rays, which in the applied form simplistically and generally speaking—both do not penetrate more than a few millimeters deep into tissue, because the radiation is absorbed in the first few millimeters of the outer layers of the skin, cavity or wound bed. In practice, this means that the radiation may penetrate deeper, but does only have a therapeutic effect in the first few millimeters. This fact renders these types of radiation suitable for, i.e., cosmetic treatments on or near the skin surface or treatment of superficial tissues also inside of the body, as the overall radiation dose which is applied as an undesirable side-effect to deeper lying living cells is neglectable, or at least tolerable, depending on the individual treatment case.

Known examples for cosmetic treatments include the treatment of scar tissue in order to smoothen or equalize the optical appearance of the respective skin region, or the desaturation of ink colors used in tattoos which the person wants to get rid of.

An example for a medical treatment is that of lesions on the skin, in particular of carcinoma. There are three main types of cells in the top layer of the skin (i.e. the epidermis): squamous cells, basal cells and melanocytes. The most common type of skin cancer is basal cell carcinoma (BCC) usually developing on sun-exposed areas such as the head and neck. Squamous cell carcinoma (SCC) also appears on sun-exposed areas of the body such as the face, ears, neck, lips, cleavage, back, legs, feet, and hands. SCC can also develop in scars or chronic skin sores and the skin of the genital area. Melanomas (cancer arising from melanocytes) are much less common than BCC and SCC. Worldwide several millions of people are diagnosed with non-melanoma skin cancer each year, and a considerable number of people die from it. Similarly other cancer types may be treated for example SCCs affecting the vagina, the female cervix, the mouth, the pharynx and larynx, colorectal cancers, esophageal carcinomas like Barrett's carcinoma, among many others.

Of particular relevance are patients bearing these cancers in the head, neck or genital area. Some of these patients are considered very severe "inoperable" cases, currently left only with inadequate or no viable treatment options resulting in high morbidity and often a psychological and economic burden. Additionally large area or multiple tumors are considered as severe in many cases even in "simple" body parts, as surgery involves complicated plastic reconstruction or tissue transplantation with high chances of failure and is often not possible at all. Treatment cost for such severe cases can be estimated to range between € 5,000 and € 120,000 (and more) depending on localization, stage of the disease, need for transplants, complications, co-morbidity, etc. Thus, means for treating such severe cases with an innovative non-invasive curative approach are urgently awaited. The gained knowledge and medical expertise can then also be applied to easier cases, other skin diseases and cosmetic applications.

One strategy for severe cases of cancer is radiation therapy using electron beams or low energy X-rays ("soft" X-rays). However, it is contraindicated for some non-melanoma skin cancers such as verrucous carcinoma (VC) and patients with genetic predisposition to skin cancer and connective tissue diseases. Further, due to the radiation burden, it is not recommended for patients younger than 60 years. The reason for these constraints is the fact that these therapies irradiate not only the tumor, but healthy surrounding and deeper tissue too. The common approach for radiotherapy implies treatment normally over 4-7 weeks in daily fractions. The only option for patients that cannot undergo such treatments or where they have failed to work is the use of chemotherapy with significant co-morbidity and only a low rate of response.

In contrast, by using radioactive material (method elsewhere also known as brachytherapy) with low penetration emissions applied directly to the abnormal skin, a very localized radiation therapy can be performed allowing for flexibility regarding the lesion extension and site. It has been demonstrated that a synthetic inert resin matrix containing the radioactive material can be effectively applied on the surface of a BCC or SCC. This "paint" dries out within a few seconds after application in a flexible film, and irradiation can be performed strictly limited to the area affected. After a short time, i.e. such as few minutes to four hours, depending on the desired irradiation dose and penetration depth, a protective foil placed between skin and the paint is used to avoid the skin to be in contact with the radioactive material and can be removed together with the hardened resin after the treatment.

As a radioactive material, various isotopes of Rhenium have proven to be viable. $^{186}$Re and $^{188}$Re are artificial isotopes that are used, for example, as radioactive tracer and for other applications in nuclear medicine. For example, the beta-emitter $^{188}$Re has proven to be a good choice as a radioactive source for radionuclide therapy. $^{188}$Re has a half-life of about 17 hours and the average penetration of its irradiation into the skin is about 2-3 mm (92% of its deposited dose is below 3 mm depth). This is sufficient to treat most BCC and SCC without damaging lower layers of the skin and underlying tissue. Besides beta-emission, $^{188}$Re also emits to about 15% gamma-irradiation of 155 keV which enables the use of standard nuclear medicine (imaging) technologies to detect potential contamination. The beta-emitter $^{186}$Re as well is a viable choice as a radioactive source for radionuclide therapy. $^{186}$Re has a half-life of about 89.25 hours and the average penetration of its irradiation into the skin is about 1-1.2 mm (94% of its deposited dose is below 1 mm depth). This is sufficient to treat thin BCC and SCC or BCC and SCC located in areas with thin skin (e.g. eye lids, ears) or mucous membranes (lips, genitals) without damaging lower layers of the underlying tissue. Besides beta-emission, $^{186}$Re also has a gamma-component at 137 keV.

The suitability of $^{188}$Re as a radioactive source has been demonstrated in an Italian study with over 350 patients (Cipriani, Cesidio, and Antioco F. Sedda: "Epidermal Radionuclide Therapy—Dermatological High-Dose-Rate Brachytherapy for the Treatment of Basal and Squamous Cell Carcinoma" In: Therapeutic Nuclear Medicine, edited by Baum, Richard P., New York: Springer, 2014), wherein a large variety of BCC and SCC forms, i.e. tumors of very large size to relapsing or recurrent forms and multifocal lesions, have been treated successfully in 98.5% of over 1,200 lesions.

However, the above described methods leave room for improvement. For example, in the above described method, the control of the uniformity of the thickness of the "paint", i.e. of the resin matrix containing the radioactive material, on the skin poses a challenge during application. Hence, it is challenging to achieve a uniform layer thickness of the paint over the whole treated skin area. This may in turn lead to the application of a non-uniform dose which may be dependent on the particular location on the skin, which is undesirable.

In view of the above and for other reasons, there is a need for the present invention.

SUMMARY OF THE INVENTION

In a first aspect, a method for producing a model for the application of radiation to a body surface area of a living being for cosmetic or therapeutic purposes is provided. The method includes defining a body surface area to which radiation shall be applied; producing a model having at least one surface which has the inverted shape of the defined body surface area, so that the model is configured to fit on the defined body surface area; and providing a radioactive isotope to the model during its production or after its production.

In a second aspect, the use of the model produced in the method of the first aspect in a cosmetic treatment is provided.

In a third aspect, a model for the application of radiation to a body surface area of a living being for cosmetic or therapeutic purposes is provided. The model includes a surface which has the inverted shape of a defined body surface area which shall be treated with radiation.

DEFINITIONS

Figure 1:
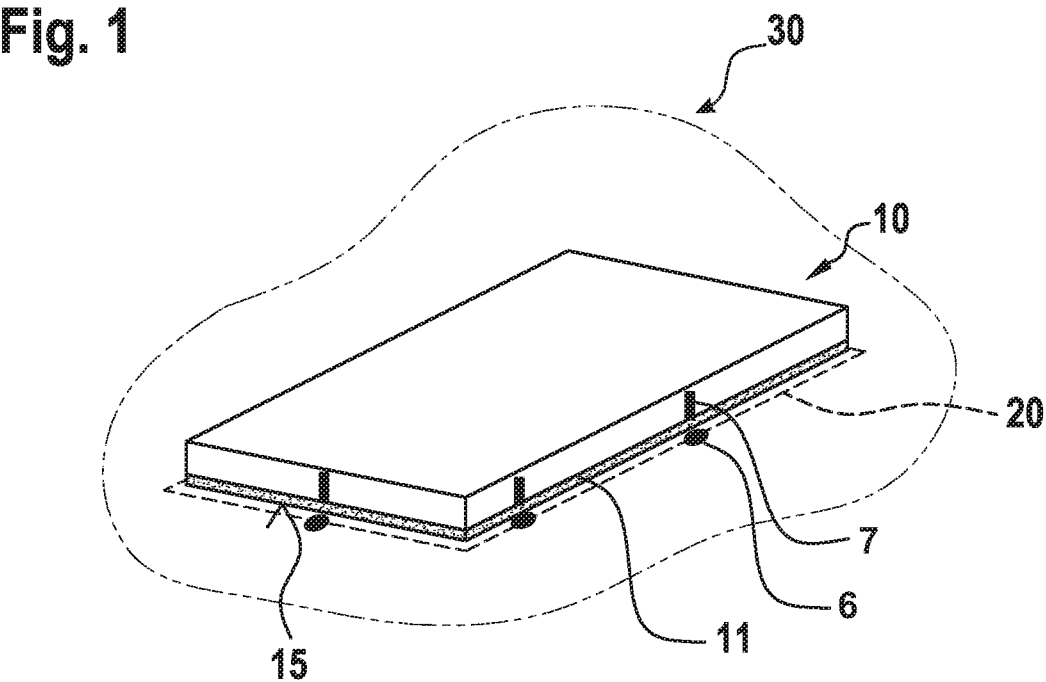
FIG. 1 schematically shows a model on a body surface area, according to embodiments.

Before the present invention is described in detail below, it is to be understood that this invention is not limited embodiments described herein. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art.

In the following, some definitions of terms frequently used in this specification are provided.

In the event of a conflict between common definitions or teachings and definitions or teachings recited in the present specification, the text of the present specification takes precedence.

In the context of the present invention, the term "particles" refers to particulate matter such as atoms, clusters of atoms or molecules of single or multiple elements. In general, there is no restriction regarding the quantity of matter forming a particle.

The term "homogeneously dispersed" as used herein refers to an emulsion in which the radioactive particles are in a continuous phase with a matrix component. In this context, the term "matrix or matrix component" refers to a carrier or a component of a carrier which is used as an auxiliary compound for taking up the activated particles according to the invention. In this respect, the term "resinous matrix" is used to refer to a semi-fluid resin.

The term "% or percentage" as used herein refers to wt % or weight percentage unless otherwise indicated.

The terms "patient" or "person to be treated", or more generally "living being", are used interchangeably herein for a person or an animal which undergoes a treatment of a body surface, and particularly of a skin area, a cavity area or an internal area reached through an incision, by applying a model according to embodiments. Thereby, it is of no relevance for the use of the term whether the treatment is intended for medical purposes, or for cosmetic, or for other purposes.

DETAILED DESCRIPTION OF THE INVENTION

In the following paragraphs different aspects of the invention are defined in more detail. These aspects are listed as specific embodiments, however, it should be understood that they may be combined in any manner and in any number to create additional embodiments. The variously described embodiments should not be construed to limit the present invention to only the explicitly described embodiments. Each aspect defined may be combined with any other aspect or aspects unless the context indicates otherwise. In particular, any feature indicated as being exemplary, preferred or advantageous may be combined with any other feature or features indicated as being exemplary, preferred or advantageous.

Embodiments pertain to a model for the application of radiation to a body surface area of a living being. Generally, the model may be used for applying radiation for cosmetic or therapeutic or other related purposes. The model comprises a first surface which has the inverted shape of a defined body surface area which shall be treated with radiation. Generally, the model has at least one first surface which is configured so that the model mechanically fits or may be fitted—with the first surface—onto a defined body region, or body part, to which radiation shall be applied, or which at least includes an area which shall be treated. It is, unless otherwise stated, generally of no particular importance in embodiments described herein, which shape or dimensions the model has, apart from it including one surface, namely the first surface, making it able to be physically fitted to the body surface area to be treated.

Generally, models according to embodiments may be used in, and methods according to embodiments may be used in, or pertain, as non-limiting examples, to the application of radiation to the skin, to parts of the surface of body cavities through natural orifices (e.g. inside of the mouth, the anus or the vagina), and to the application of radiation to surfaces inside of the body accessible through an incision, e.g. a tumor bed after the removal of a breast tumor, or the surface of the liver accessible through a port during a laparoscopic surgery. Hence, the term "body surface" as used throughout this application may be an outer surface of a body, or generally a surface inside of the body.

For example, the model can be a kind of plate, which may in embodiments be flexible. In other embodiments the plate may include a rigid material such as a thin plastic material of, e.g., from a few microns to a few millimeters thickness. In other embodiments, the model has a 3D shape. As used herein, this is intended to mean that the model has a considerable elongation in each of the three Cartesian dimensions, which will be defined and laid out in greater detail further below.

In embodiments, the model generally includes a radioactive material at the point in time when the model is applied to the body surface area to be treated. The radioactive material—which typically may include one of the Rhenium isotopes named earlier, other isotopes specified further below or different, further isotopes—is typically located in a thin layer at, or close to, the first surface of the model, which will be fitted to the body surface area to be treated. That is, the radioactive material may be part of a radioactive layer including a different basic material than the body of the model. The radioactive layer may thus comprise a different basic (or: matrix) material, in which the radioactive material is dispersed, than the body of the model itself. Generally, the radioactive material (or radioactive layer) may be added to the model during the production step of the body of the model itself, or also at a phase when the body of the model is already produced. In other variants, the still non-radioactive isotope is added to the model during or after production of the model body, but the isotope is only activated (i.e., made to be radioactive) by activation in a nuclear reactor (e.g. a neutron source) or by another radiation source to which the model is exposed, for example. In most embodiments, the radioactive material is concentrated in a radioactive layer at a first surface of the model, in other embodiments the radioactive material may also be distributed over the whole model, or only over certain parts of the model, optionally also with varying concentration in different regions of the model.

In FIG. 1, a model 10 according to embodiments, for the application of radiation to a body surface area 20 of a living being 30 for cosmetic or therapeutic purposes is shown. The model 10 comprises a first surface 15 which has the inverted shape of a body surface area 20 which shall be treated with radiation emitted by the model 10. In FIG. 1, the model 10 has—as a non-limiting example—a substantially planar shape. When the material of the body of the model 10 is chosen to have sufficient flexibility, the model 10 may be fitted to a slight curvature of the body surface area 20, so that there is a tight fit and no or a small air gap between the first surface 15 and the body surface area 20. The radioactive material is typically provided in a radioactive layer 11 facing the body surface area 20. In this setup the radioactive material is bound to the model 10, such that no, or only minute, diffusion from the model 10 to the living being 30 takes place. In some embodiments, the determined target area (body surface area 20) may be physically marked on the surface, such as is shown in FIG. 1 with asymmetrical marking points 6 on the skin of the living being 30. This can be carried out, e.g. by manually using a standard pen for medical markings. This marking with asymmetric marking points can be used for the placement/positioning of the model 10. In some embodiments, the marked area is then copied on a surface such as a paper, or a plastic foil, which includes dimensional information. The copied treatment area is scanned into an electronic data format, resulting in an electronic representation of the body surface area 20 in a data model 13 (see FIG. 3), in some embodiments including a representation of marking points 6 or markers 7 which may then be added to model 10 during manufacturing. The inclusion of the positions of marking points 6 or markers 7 in a data model 13 used for production of model 10, which then includes markers 7, may be employed in all embodiments described herein, where technically feasible.

Figure 2:
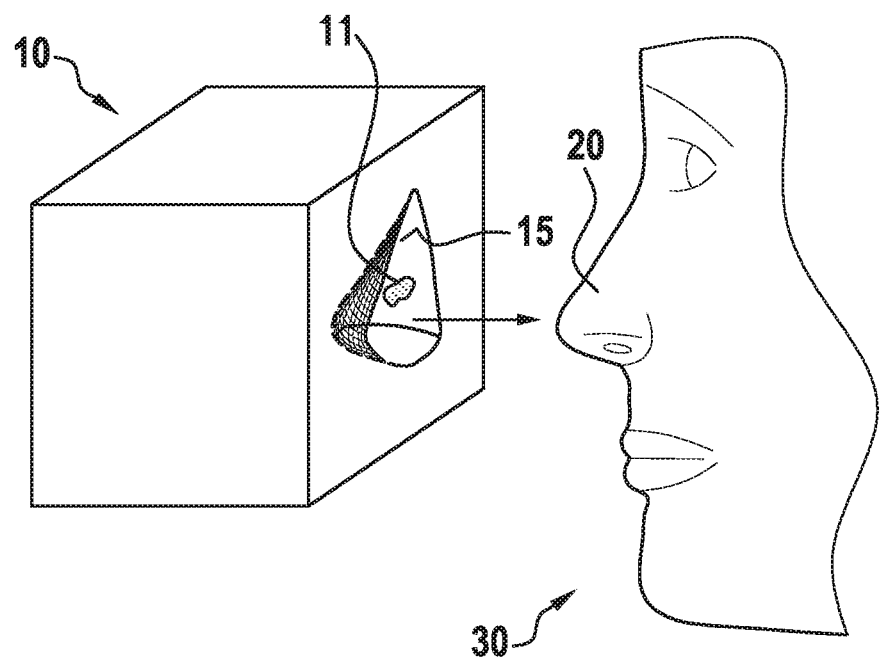
FIG. 2 schematically shows a further model on a body surface area, according to embodiments.

In FIG. 2, a model 10 according to further embodiments is shown. Thereby, the model 10 has—exemplarily—a body substantially resembling a cube, whereby the first surface 15 has the inverted shape of the body surface area 20 being substantially the surface of the nose of the living being (or patient) 30 to be treated. The radioactive layer 11 is in this case only provided as a part or subarea on the first surface 15 being the inverted form of the body surface area 20 to be treated.

It goes without saying that the model 10 of FIG. 2 might have very different outer shapes—apart from the first surface 15—than the one exemplarily shown. For example, the model 10 may have any (preferably simple for reasons of production) geometrical shape, such as a cube, a cylinder, a sphere, or combinations thereof. The only prerequisite is that the first surface 15, having the inverted shape of the body surface area 20 to be treated, fits completely into the model 10. In some cases, the dimensions of the radioactive layer 11 may be smaller than the first surface 15, because the first surface 15 is designed to cover a skin area which is bigger than the actually treated skin area, such as exemplarily shown in FIG. 2.

The body of model 10 may include a variety of materials, such as polymers (plastic), ceramic, a gel, a modeling compound a dough, orthopedic cast, or a metal. Basically, the material of model 10 needs only be hard enough, such that it can be molded, while keeping its shape at least during the duration of the treatment, which is typically at most in the range up to some hours. Alternatively the body of model 10 may be of a rigid material that gets processed in order to obtain the inverted shape of the body surface area for example by using a CNC milling machine. A thin polymeric layer may be provided between the model 10 and the body surface area 20 to be treated, in order to physically separate the radioactive material, respectively the matrix material of the radioactive layer 11, and the skin at the body surface area avoiding as such potential radioactive contamination or incorporation by the patient.

It is understood that in most use cases, the model 10 will be produced for the individual use case, or treatment case, because the shape, size and in most cases 3D shape of the first surface 15 need to be designed and adapted for the individual treatment. To this end, in a first step, the body surface area 20 to which radiation shall be applied, is typically defined by a human operator. For cases of cosmetic treatment only, this step is evidently based on defining the target area for the treatment. This may e.g. be a tattoo, the colours of which shall be desaturated. Another application may be the treatment of scar tissue, e.g. keloids, stemming from a previous surgery or injury, for example.

In embodiments, the model 10 may be produced mainly manually. To this end, there basically are two possibilities. Firstly, a formable material such as plaster or a gel may be used to make an inverted cast of the area to be treated including body surface area 20. The formable material than cures (or undergoes a different solidifying process, such as plaster). The resulting solid body, including first surface 15 having the inverted shape of the body surface area 20, can then be used to further produce a mould in which the model 10 is cast. Alternatively, the cast can directly be employed as the model 10. In this case, the radioactive layer 11 is applied to the model 10 at the first surface 15.

If the treatment is for medical purposes, i.e. treating a lesion on the skin, a cavity or an inner body surface, the process of defining the body surface area 20 may comprise more complex steps. The area may be defined, typically under supervision by a medical doctor, employing clinical examination, dermatoscopy, biopsy or a plurality of biopsies. Further, OCT, CFLSM, two-photon microscopy, Raman microscopy, ultrasound examination, autofluorescence, (narrow-band) infrared imaging, X-rays, CT, MRI, terahertz imaging, heat imaging or further, similar methods may be applied. Thereby, the area of the lesion is defined, regarding the lesion alone or the lesion with a security margin around it. Depending on the medical particulars, also a depth of the lesion below the surface which can be non-uniform and thus vary over the treated area is determined in or after this process.

Figure 3:
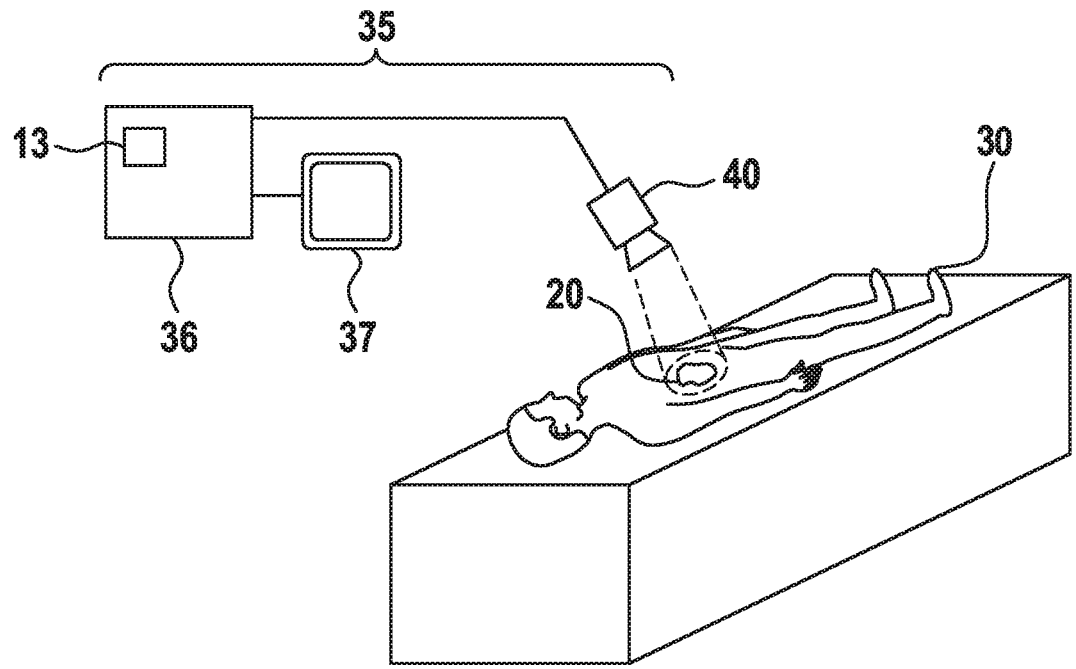
FIG. 3 schematically shows the acquisition of data on a body surface area to be treated, as employed in embodiments.

In other embodiments such as exemplarily shown in FIG. 3, an integrated imaging system 35 is used. Using the latter, an operator can mark with semi-automatic or fully automatic assistance of the computer-assisted, integrated imaging system 35 the body surface area 20 of the living being 30 on the screen 37 of the integrated imaging system 35. When the body surface area 20 has a considerable (i.e., non-neglectable) non-planar shape, this shape is typically acquired in three dimensions (3D), such that a 3D model of the body surface area 20 is acquired and stored in the integrated imaging system 35. Depending on the part of the anatomy to be treated (i.e., planar sections of the back of the patient), it may be sufficient to acquire merely the dimensions of the body surface area 20 in 2D. The steps just described may be carried out employing equipment and methods for image recognition and 3D modelling, which are per se basically known to the skilled person. During the step of acquiring information about the shape and geometry of the defined body surface area 20, at least one data acquisition device 40 chosen from the following list is typically employed: at least one 2D cameras, a 3D camera (as exemplarily shown in FIG. 3), a laser scanner, a structured light scanner, a mold, a measuring arm, a robotic arm, a sonar system, a pressure based acquisition system, a 2D scanner or a combination of the former.

After information about the shape and geometry of the body surface area 20 was obtained as described above, a data model 13 of the body surface area 20 is created and stored in the data processing unit 36 of the integrated imaging system 35. The data model may be a representation in one dimension (meaning, along a line), in two dimensions or in three dimensions, and typically includes size information.

In a further step, the information on the body surface area 20 stored in the data model 13 is employed to produce the model 10. Thereby, two cases are possible, which are laid out in the following.

In the first case, when the body surface area 20 has a basically planar shape, or has a shape with a curvature which may, e.g. be equalized by a slight bending of the model 10, then the first surface 15 can, for example, be printed on a carrier material resulting in a model 10 such as shown in FIG. 1.

Figure 4:
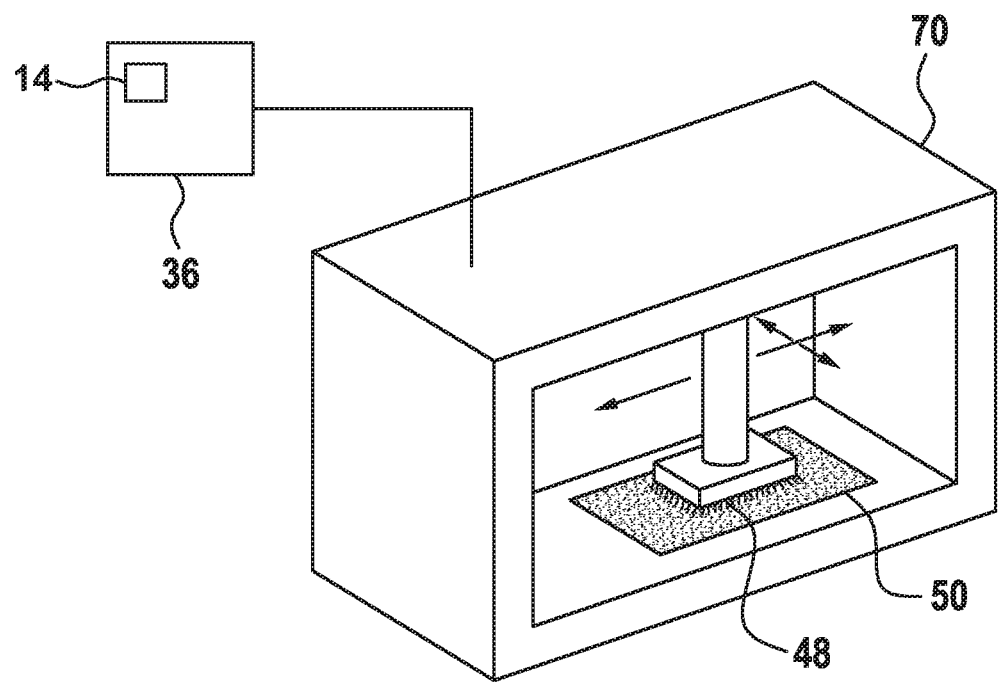
FIG. 4 schematically shows the production of a model as of FIG. 1, according to embodiments.

As shown in FIG. 4, in the above case, only the size and dimension information of the first surface 15 is typically transferred to a 2D printer 70. The 2D printer 70 prints the radioactive material, typically dispersed in an ink 48, onto the carrier material 50. The carrier material may be from a wide range of materials, e.g. plastic, silicon, rubber, or leather, etc. The carrier material can either be provided to be sufficiently thick in order to block the beta and/or "soft" gamma radiation from the ink in a (undesired) direction away from the area to be treated, and/or can include compounds which help to stop the beta and/or "soft" gamma radiation.

In embodiments, the thickness of the ink 48 deposition is thereby calculated from the intended activity per area. Alternatively different inks having different activity concentrations may be used. Also using different radioactive isotopes in different inks is possible. The 2D printer 70 is controlled by a data processing unit 36, which delivers the data about the shape and dimensions from the data model 13. The data processing unit 36 may be the one described with respect to FIG. 3. It may also comprise an algorithm to calculate the necessary deposition thickness of the ink 48 on the carrier material 50, or the deposition thickness can be manually calculated and entered by an operator. The carrier material 50 may be cut previous to the printing process in order to fit to the dimensions of the first surface 15. Alternatively, it may be cut after the printing process. It may be cut to have a margin with a defined width around the first surface 15, or may be kept to have a standard (rectangular) shape with the first surface 15 printed thereon. The layer of deposited ink forms, after drying, the radioactive layer 11 as described with respect to FIG. 1, while the carrier material 50 and the ink 48 together form the model 10 of FIG. 1. The distribution of the radioactive material in the radioactive layer 11 must not be necessarily homogenous if a non-homogeneous distribution is desired. This can be the case of a large tumor which have variable thickness and where the desired radiation dose varies over the area accordingly.

Figure 5:
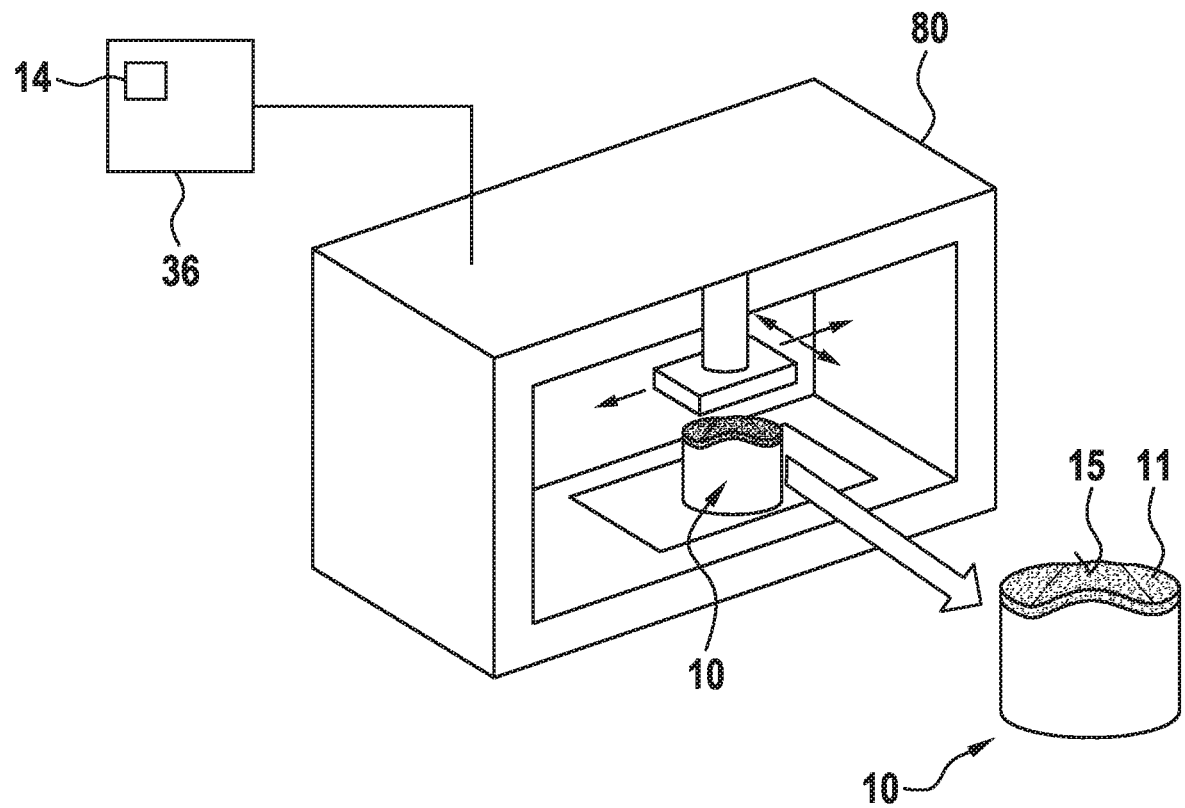
FIG. 5 schematically shows the production of a model according to embodiments.
Figure 6:
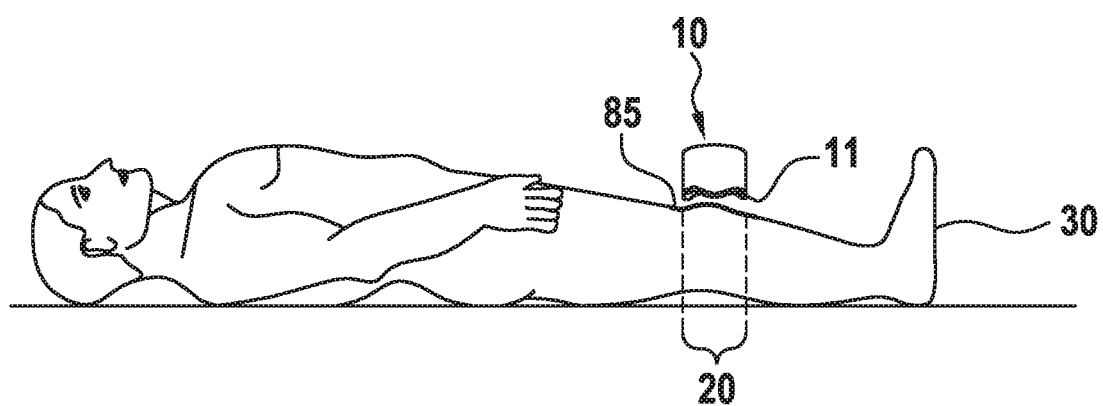
FIG. 6 schematically shows the use of a model according to embodiments.

In the second case, the body surface area 20 has a significantly non-planar shape (see e.g. FIG. 5 and FIG. 6). The first surface 15 is in this case produced as one face of a model 10 being a solid body with three dimensions. The data model 13 in this case includes a representation of the first surface 15, which is an inverted (by calculation in the data processing unit 36) shape of the body surface area 20 to be treated. In order to produce a model 10 which can be fitted on the body surface area to be treated, the first surface 15 is integrated into a 3D body 14 being a data model. In a simple example, this 3D body 14 may have the basic shape of a cube such as shown in FIG. 2, which at one of its faces is at least partly shaped according to the first surface 15. It is understood that the actual shape and size of the 3D body 14 can be varied significantly. The main prerequisite is, that it is suitably shaped and large enough to include the entire first surface 15 as one of its faces.

In order to create the 3D body 14 from the data model 13 including the first surface 15, there may be an algorithm integrated into data processing unit 36. There may be a graphical user interface provided on the screen 37, which is provided to assist an operator with an algorithm in creating a suitable 3D body which will subsequently be produced into model 10.

Once the 3D body 14—as a data model—has been created from the first surface 15 embodied in the data model 13, the data of the 3D body 14 is transferred from the data processing unit 36 to a model creation device 80. The model creation device 80 is employed to produce the model 10 as an actual physical representation of the 3D body 14, which is schematically shown in FIG. 5.

From a point of view of production of the model 10 from the data of the 3D body 14, the model creation device 80 may in embodiments be any device or instance which is suitable to physically produce the model 10 from the 3D body 14. Hence, the skilled person will readily understand that any technique suitable for creating physical bodies from 3D data might be employed according to embodiments. That is, a wide range of techniques may be employed for producing the model 10 by using the model creation device 80, which may for example include a 1D printer, a 2D printer, a 3D printer, a laser rapid prototyping machine, a milling machine, a lathe, a laser cutting machine, a water cutting machine, a block-based building system, a molding device, or a suitable combination of the former.

Partly departing from the standard techniques for producing 3D models, the step of adding the radioactive material to the model 10 may, according to embodiments, be carried out in a number of different ways. Depending on the manner of adding the radioactive isotope to the model, precautions or safe handling procedures for radioactive materials have to be employed at various stages of the process. Basically, the radioactive material can be built into the model 10 already during its production, respectively formation. This includes that a matrix material including the radioactive material is used in the model creation device 80, e.g. a 3D printer, meaning that the device, or at least parts thereof, partly becomes radioactive itself. That is, if for example a 3D printer is used as the model creation device 80, the 3D printer needs to process a radioactive material in the 3D printing process, which in the model is part of the radioactive layer 11 (see FIG. 2). This can be implemented for example by using a radioactive color.

In a further variant according to embodiments, the model 10 is produced without the radioactive layer 11, that is, a thickness for the radioactive layer is spared in the production process. The radioactive layer 11, meaning the matrix material and the embedded radioactive material, are added to the model 10 in a subsequent application step. This can also be done if the mould is done manually, as was described previously.

A further variant includes that the model 10 is produced with the first surface 15 comprising the radioactive layer 11 in a form which only becomes radioactive after activating it in a nuclear reactor (e.g. a neutron source), or by another source of radiation. In this manner, the model may be produced in a surroundings without the need for radiation protection.

In short, the radioactive isotope, or radioactive material, may be provided to the model 10 during its production, or after its production. As an example, a 3D printer is used to print the non-radioactive part of the model 10, while subsequently using a printing material comprising the radioactive material for printing the radioactive layer 11 which forms first surface 15. Alternatively, the radioactive layer 11 may be applied applying a thin layer of a material comprising a radioactive isotope, after the model 10 has been produced, preferably a radioactive solution, suspension or spray, radioactive particles or a combination of them. Finally, the produced (non-radioactive) model 10 may be exposed to a radiation source in order to activate an isotope in the model. It is important to consider that in such situation the chemical composition of the model must be known and extremely pure in order to avoid the activation of impurities that may result in undesired sources of radiation (e.g. long half-life isotopes, high energy radiation isotopes, etc).

Thereby, the local concentration of the radioactivity, that is of the radioactive isotope, in the model 10 may be provided to vary locally over the model, for example by providing a varying thickness of layer 11. Thereby, a varying dose of radiation applied to the body surface area 20 can be achieved, which can typically be defined on the basis of the parameters of the individual case of radiation application.

The radioactive isotope employed in the radioactive layer 11 is in embodiments typically chosen in order to decay mainly emitting one of the following radiation types: beta radiation, soft X-rays, or soft gamma rays, wherein "soft" is intended to mean an energy of 20 keV or smaller. Generally, in embodiments described herein, any radioactive isotope can be suitable which deposits equal or more than 80% of its energy within about 5 mm of penetration depth in the skin of a living being 30. A non-limiting choice of suitable radioactive isotopes are from the following list which comprises $^{186}$Re, $^{188}$Re, $^{90}$Y, $^{32}$P, $^{165}$Dy, $^{103}$Pl, $^{125}$I, and $^{166}$Ho. Also combinations of the former or with/from other radioactive isotopes may be suitable. The radioactive material can have the form of pre-prepared, formed particles. These particles can in some embodiments be pre-produced first and activated after producing the model 10, as was described herein. The radioactivity, in the form of the radioactive isotope, can be absorbed on other particles, such as, e.g., titanium particles. Generally, the radioactivity can be in the forms of particles, in ionic form, or in a compound of the radioactive element. The former are then dispersed in a radioactive ink, or mixed in a matrix material such as a polymer, e.g., a resin. The latter is then, for example, processed by the model creation device 80 as exemplarily shown in FIG. 5.

Generally, the model 10 as disclosed herein can, according to embodiments, be employed in a cosmetic treatment of the skin, or for the treatment of a lesion on a body surface, i.e. on the skin, on a part of a cavity or on an inner body surface. Typical cosmetic treatments include desaturating the colour of tattoos, or treating scar tissue. The typical time for placing the model 10 on the patient may range from several minutes up to some hours, depending on the nature of the treatment and the applied dose. When, for example, lesions in the region of the head shall be treated, an additional mask may be applied to other parts of the head, so that an unwanted radiation exposure of other areas is minimized. This is particularly true for the treatment of the nose area, in which case the eyes can be so protected.

Regions on the head for which the disclosed method and treatment can be particularly useful, include the outer ears, the nose, and other parts of the face. The treatment of lesions in the female cervix or on the tumor bed after a tumor resection procedure are also very promising.

Generally, in embodiments, a thin polymer film 85 may be applied between the body surface area 20 to be treated and the model 10, which is schematically shown in FIG. 6. The thin polymer film 85 may be applied to the defined body surface area 20 prior to placing the model 10 thereon. Also, the polymer film 85 may be applied to the model 10 prior to placing it on the defined body surface area 20. The thin polymer film may be applied by, as non-limiting examples, spraying, painting, casting the film, or applying a ready-made plastic foil or film to the skin on the body surface area 20. If no such a separation layer is used, the radioactive material is preferably bound to the matrix, such that diffusion to the living being, sublimation or evaporation is avoided, minimizing the risk of contamination or incorporation.

When the model 10 is produced according to one of the methods disclosed herein, it has to be aligned on the body surface area 20. Thereby, various methods may be applied in embodiments, which include as non-limiting examples: Marking points 6 can be placed on the skin of the body surface area 20, which mark the outline of the model 10 when placed on the skin. Optionally, markers 7 may also be applied on the model 10 in order to match them with the marking points 6 on the skin, such as was shown in FIG. 1. In case that the model 10 is a 3D model such as shown in FIG. 2, the model may be fitted by an operator according to the geometrical fit of the model 10 to the defined body surface area 20. The latter may be accompanied by a visual control and/or pressure control by an operator, or in embodiments by a robot arm. a distance control, a conductivity control, or the use of natural anatomical landmarks.

Thereby, the model may be configured such that only a part of the body surface area 20 to be treated is covered by the model 10. For example, this may be viable when a first a part of the lesion shall be treated first, and only later another part. Also, if only a part of a lesion—or a part of a scar, for example—cannot be treated effectively by applying radiation, the respective part of the lesion or scar will previously or subsequently be treated with another method.

Figure 7:
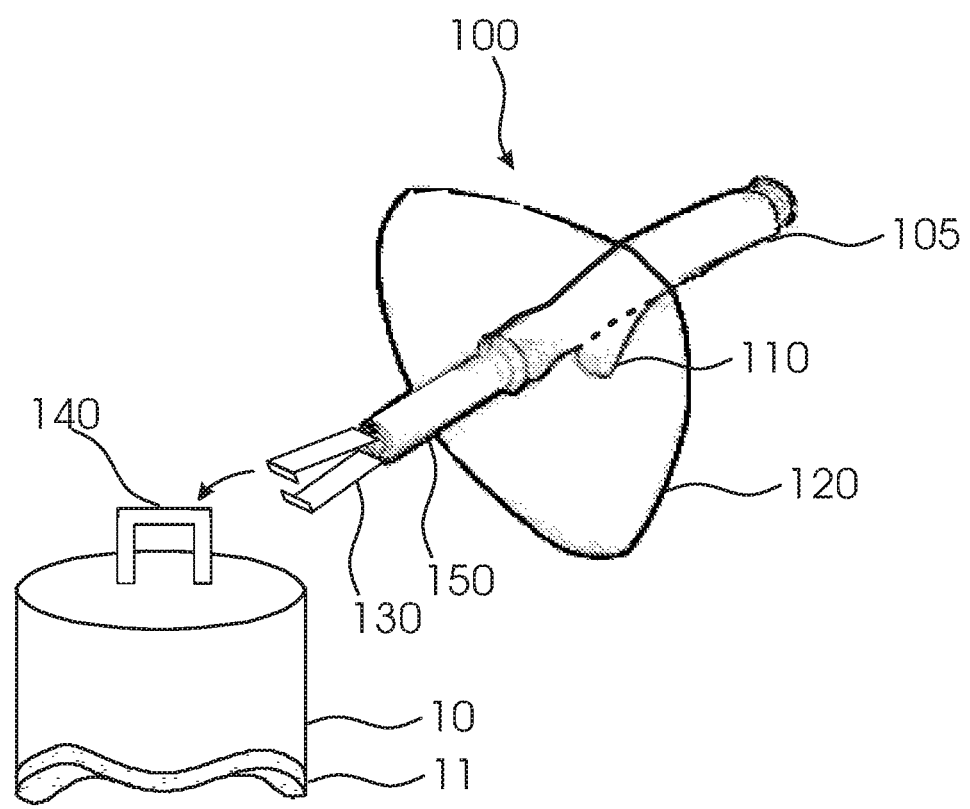
FIG. 7 schematically shows a handling tool for handling a model according to embodiments.

Once the model 10 has been produced and provided with the radioactive material, e.g., in the form of radioactive layer 11, there is a question of radiation protection of an operator handling the model 10. While during production of the model, radiation protection can be achieved with relatively simple measures, during the treatment, the operator is necessarily in relatively close contact with the model 10. Thereby, mainly the process of taking the model out of a protection container, for example, and placing it at the designated position on the patient's body has to be accounted for. In FIG. 7, a handling tool 100 with radiation protection is shown. The handling tool 100 has a handle 105 and a front part 150. At the tip of the front part, a holding mechanism 130 is provided, which may, as non-limiting examples, have the shape of a pliers or a gripper. The holding mechanism is activated, e.g., by a trigger 110 provided at, and/or integrated with, the handle 105. Between the handle 105 and the front part 150, an optional shield 120 for the hand and the person behind is provided, which may typically comprise plastic or metal to shield the radiation emitted from the model 10. With the handling tool 100, an operator may grip a model 10, safely carry it, and place it on or at the living being 30, and release it from the handling tool 100. Typically, a holding element 140 is mounted at the model for this purpose, which may be made from metal or a polymer, for example. The holding element 140 may be added to the model 10 during the production process, or it may be formed as an integral part of model 10 during the production process, e.g., by 3D printing. The holding element 140 is typically shaped to engage or to fit with the holding mechanism 130.

The skilled person will readily understand that there are many variations in the concrete design and function of the handling tool 100, which are also regarded to fall under the scope of this disclosure. The handling tool 100 may be used in conjunction with any one of the methods disclosed herein, or combinations thereof.

The invention claimed is:

1. A method for producing a model for the application of radiation to a body surface area of a living being for cosmetic or therapeutic purposes, the method comprising:
    defining a body surface area to which radiation shall be applied;
    producing a model having at least one first surface which has the inverted shape of the defined body surface area, so that the model is configured to fit on the defined body surface area;
    providing a non-radioactive isotope, which can be activated by a radiation source, to the model during its production,
    providing the non-radioactive isotope to only parts of the model corresponding to the body surface area to be treated, wherein the parts of the model provided with the non-radioactive isotope do not cover the whole model,
    exposing the produced model to the radiation source in order to activate the isotope in the model.

2. The method of claim 1, wherein producing the model comprises: creating the model having at least one first surface which has the inverted shape of the defined body surface area, in at least one of:
    in 1D,
    in 2D,
    in 3D.

3. The method of claim 1, wherein producing the model further comprises:
    producing a mold and subsequently casting the model in the mold, or
    producing the model by using a model creation device comprising at least one of: a 1D printer, a 2D printer, a 3D printer, a laser rapid prototyping machine, a milling machine, a lathe, a laser cutting machine, a water cutting machine, a block-based building system, molding or a plurality of them or any combination of the former.

4. The method of claim 1, wherein the concentration of the radioactivity in the model is provided to vary locally over the model to achieve the aim of varying doses of applied radiation, defined on the basis of the parameters of the individual case of radiation application.

5. The method of claim 1, wherein producing the model comprises:
    acquiring information about the shape and geometry of the defined body surface area, and creating and storing a data model of the defined body surface area in one, two or three dimensions on a data processing unit.

6. The method of claim 5, wherein acquiring information about the shape and geometry of the defined body surface area comprises using a data acquisition device being at least one of: a 2D camera, a 3D camera, a laser scanner, a structured light scanner, a mold, a measuring arm, a robotic arm, a sonar system, a pressure based acquisition system, a 2D scanner, or a plurality or any combination of the former.

7. The method of claim 1, wherein the non-radioactive isotope is chosen, when activated, to decay mainly emitting one of: beta radiation, soft X-rays, soft gamma rays, any radioactive radiation depositing at least 80% of its energy within 5 mm of penetration in a living being.

8. The method of claim 7, wherein the non-radioactive isotope is chosen, such that when activated, is from $^{186}$Re, $^{188}$Re, $^{90}$Y, $^{32}$P, $^{165}$Dy, $^{103}$Pl, $^{125}$I, and $^{166}$Ho.

9. The method of claim 1, further comprising aligning the model on the defined body surface and cosmetically treating the skin.

10. The method of claim 9, further comprising aligning the model on the defined body surface area using at least one of the following:
  a. markers on the skin and optionally on the model,
  b. the geometrical fit of the model to the defined body surface area,
  c. a visual control or pressure control,
  d. a distance control,
  e. a conductivity control,
  f anatomical landmarks.

11. The method of claim 9, wherein the cosmetic treatment comprises:
  a. desaturating the colour of tattoos, or
  b. treating scar tissue.

12. The method of claim 9, further comprising applying a polymer film to at least the defined body surface area prior to placing the model.

13. The method of claim 12, wherein the application of the thin polymer film includes at least one of: spraying a film, painting a film, and casting a film, or applying a plastic foil, or applying a film.

14. A model for the application of radiation to a body surface area of a living being for cosmetic or therapeutic purposes, wherein the model comprises a first surface which has an inverted shape of a defined body surface area to be treated with radiation, wherein the model has a simple geometrical shape, which, at one of its sides, comprises a first surface which has the inverted shape of a defined body surface area, wherein the model comprises a non-radioactive isotope which can be activated by a radiation source, wherein only parts of the model corresponding to the body surface area to be treated is provided with the non-radioactive isotope, and wherein the parts of the model provided with the non-radioactive isotope do not cover the whole model.

15. The model of claim 14, wherein the model comprises at least one of: a polymer, a ceramic, a gel, a modeling compound, a dough, orthopedic cast, a metal, and any material soft enough to be molded, while it keeps its shape at least during the duration of the treatment, and/or a mix of any of the former, and/or wherein the model comprises rigid material that is processed in order to obtain the inverted shape of the body surface area.

16. The model of claim 14, further comprising a polymeric layer between the model and the body surface area of a living being.

17. The model of claim 14, wherein the simple geometrical shape is a cube, a cylinder, a sphere, or combinations thereof.

* * * * *